United States Patent [19]

Woznicki et al.

[11] Patent Number: 4,475,919

[45] Date of Patent: Oct. 9, 1984

[54] COLORED MEDICINAL TABLET, NATURAL COLOR PIGMENT AND METHOD FOR USING THE PIGMENT IN COLORING FOOD, DRUG AND COSMETIC PRODUCTS

[75] Inventors: Edward J. Woznicki, Douglasville; Lawrence J. Rosania, North Wales; Keith Marshall, Ft. Washington, all of Pa.

[73] Assignee: Colorcon, Inc., West Point, Pa.

[21] Appl. No.: 337,379

[22] Filed: Jan. 6, 1982

Related U.S. Application Data

[60] Division of Ser. No. 144,617, Apr. 28, 1980, Pat. No. 4,336,244, which is a continuation of Ser. No. 837,301, Sep. 27, 1977, Pat. No. 4,274,830.

[51] Int. Cl.$^3$ .............................................. D06P 3/60
[52] U.S. Cl. ......................................... 8/518; 8/646; 426/250; 426/540
[58] Field of Search .................... 8/518, 646; 426/250, 426/540

[56] References Cited

U.S. PATENT DOCUMENTS 3,162,541 12/1964 Battista ................................ 523/205
4,263,333 4/1981 Maing et al. ......................... 426/250

*Primary Examiner*—Maria Parrish Tungol
*Attorney, Agent, or Firm*—John F. A. Earley

[57] ABSTRACT

A pharmaceutical tablet consists of a substrate containing a medicament and may be covered with a coating, said coating including a pigment comprising a natural water insoluble edible powder dyed with an edible natural dye. The pigment for coloring the tablet, or other pharmaceutical products, as well as food and cosmetics, is made by suspending a natural water insoluble edible powdered substrate in an aqueous vehicle and dyeing the suspended powdered substrate with an edible natural dye. The liquid is removed to obtain the dry pigment powder of the invention which then can be suspended in a suspending medium and used for coating products to be colored such as food, drug and cosmetic products.

19 Claims, No Drawings

COLORED MEDICINAL TABLET, NATURAL COLOR PIGMENT AND METHOD FOR USING THE PIGMENT IN COLORING FOOD, DRUG AND COSMETIC PRODUCTS

CROSS-REFERENCE TO RELATED APPLICATIONS

This is a divisioan of application Ser. No. 144,617, filed Apr. 28, 1980, now U.S. Pat. No. 4,336,244, which is a continuation of Ser. No. 837,301, filed Sept. 27, 1977, which issued as U.S. Pat. No. 4,274,830 on June 23, 1981.

BACKGROUND OF THE INVENTION

This invention relates to dry edible, natural color pigments that at the present time do not require certification by the Food and Drug Administration since they utilize natural ingredients. These natural dye pigments simulate and are substitutes for FD&C and D&C lakes that are used for coloring food, drugs and cosmetics. Such lakes, and the color coating of pharmcaeuticals, confectionery, and food, are discussed in Colorcon Incorporated U.S. Pat. Nos. 3,909,284 issued Sept. 30, 1975, and 3,576,663 issued Apr. 27, 1971, and the references cited therein, all of which are incorporated herein by reference.

With the Food and Drug Administration re-examining its listed and approved FD&C and D&C lakes and withdrawing approval, considering withdrawing approval or introducing restrictions and new regulation for such lakes, there has been a demand in the food, drug and cosmetic industries for pigments that simulate closely and may be substituted for any lakes that the Food and Drug Administration may de-list or restrict. Since such de-listing may occur without very much advance notice, it is also desirable to provide a suitable substitute that may be used immediately, and that does not require submission to the Food and Drug Administration for certification.

Natural dyes such as curcumin and grape skin extract have been used for a very long time. However, they have not been used successfully to form pigments useful for coloring food, drug and cosmetic products. For example, it is not practical to use them to make the llakes employing an alumina hydrate slurry in accordance with the method of U.S. Pat. No. 3,909,284 since at best only very weak colors are obtained. Unexpetedly, the use of natural dyes together with the substrate powders of the invention and dyeing aids produce excellent pigments for their intended purpose. Not only are the pigments of high intensity but they do not bleed in water. Further, the invention has an advantage not heretofore acheived with natural pigments in that FD&C and D&C lakes can be closely simulated.

SUMMARY OF THE INVENTION

A pharmaceutical tablet has a substrate containing a medicament and may be coated, said coating including a pigment comprising a natural edible powder dyed with an edible natural dye. The pigment for coloring the tablet, or other pharmaceutical products, as well as food and cosmetics, is made by suspending a natural water insoluble edible powder in an aqueous vehicle and dyeing the suspended powder with an edible natural dye. The liquid is removed to obtain the dry pigment powder of the invention which then can be suspended in a suspending medium and used for coating products to be colored such as food, drug and cosmetic products.

DETAILED DESCRIPTION OF THE INVENTION

In carrying out the method of the invention, a natural water insoluble edible powder is suspended in a liquid. Exemplary of the powders are water insoluble powders of cellulose, microcrystalline cellulose, cellulose derivatives, for example, ethyl cellulose, and starch and starch derivatives.

Advantageously the particles of powder will be in the range of from about 1 to about 50 microns. While the amount of powder for a given amount of water will vary widely, it is preferred that the powder be from about 2% to about 15% (W/V).

Advantageously, the liquid suspending medium may be water, or an aqueous solution, for example, an acid or a base to achieve a specific pH.

The suspended powdered substrate is then dyed with an edible natural dye, for example, curcumin, turmeric, or an anthocyanin such as those contained in commercial grape skin extract. The dye may be added directly to the liquid in which the powder is suspended or may be first placed in a solvent to form a dye solution which is then added to the suspended powder. Typically the solvent will be water but other solvents such as, for example, methyl alcohol, or ethyl alcohol may be used.

Advantageously an agent is employed to fix the dye onto the powder. Exemplary of these against are metal salts such as sodium chloride, aluminum chloride, and aluminum sulfate. Inorganic acids such as, for example, hydrochloric acid may also be employed. Except in the case of the inorganic acids, the fixing agent may be in an amount equal to form about 0.1 to about 10% by weight of the powder in suspension. Where the acidity of the suspension is relied upon to fix the dye to the powder through the use of an inorganic acid, it is preferred to have the pH from about 1.0 to about 5.0.

The dye per se or in solution is advantageously added to the suspension of the powder slowly while the suspension is stirred. The stirring is continued after all of the dye has been added for a sufficient period of time to fix the dye to the powder, generally from about 1 to 2 hours, depending on the particular dye. The suspension is then filtered and the recovered powder washed with water and dried to obtain the powdered natural dye pigment which has a particle size in the range of from about 1 micron to about 50 microns. While the powdered pigment can be air dried it is advantageous to carry out the drying in a mechanical convection oven at an elevated temperature of, for example, from about 40° C. to about 50° C.

Following the above method, FD&C and D&C lakes can be closely simulated using one or a mixture of pigments.

A pigment made in accordance with the above method is normally placed in a suspending medium to form a stock suspension which is further diluted prior to application to the product to be colored. Typically the suspending medium is an aqueous medium containing simple syrup U.S.P. and the pigment is present in an amount of from about 10% to about 25% (W/V). The dilution before coloring the selected product may be carried out with any standard syrup, for example, simple syrup, U.S.P., the amount of dilution depending upon the intensity of color desired. Advantageously the diluted suspending medium contains pigment in the amount of from about 1% to about 5% (W/V). Then, for example, tablets are readily coated by placing the tablets in a coating pan and rotated. The diluted stock solution containing the pigment is added in a quantity sufficient to cover the tablets. The covered tablets are dried and the operation repeated until the tablets have the desired color.

The invention will be further clarified by the following specific examples:

EXAMPLE I 100 g of finely powdered microcrystalline cellulose is suspended in 1800 ml of water. 50 g of a 30% (W/V) aluminum chloride in solution in water is added to the cellulose suspension and the suspension heated to 50° C. 10 g of curcumin is dissolved in 800 ml of water containing 3.2 g of sodium hydroxide to form a dye solution. The dye solution is then added in a fine stream to the microcrystalline cellulose suspension while stirring the suspension rapidly. Stirring is continued until all the curcumin is attached to the microcrystalline cellulose particles (60 minutes). The slurry is filtered, washed with water to remove any free dye not attached to the cellulose particles, and dried at 50° C. in a hot air oven to obtain a powdered natural dye pigment that simulates and may be substituted for FD&C Yellow No. 5 Aluminum Lake.

EXAMPLE II 100 g of finely powdered cellulose is suspended in 1800 ml of water. 15 g of aluminum sulfate powder is dissolved in the cellulose suspension and the suspension is then heated to about 50° C. 5 g turmeric is dissolved in 800 ml ethyl alcohol forming a dye solution. The turmeric dye solution is then added in a fine stream to the cellulose suspension while stirring the suspension rapidly. Stirring is continued until all the turmeric is attached to the cellulose particles (60 minutes). The slurry is filtered, washed with water and dried at 50° C. in a hot air oven, to obtain a powdered natural dye pigment of yellow-orange color.

EXAMPLE III 100 g of finely powdered cellulose is suspended in 1800 ml of water. 10 g of water soluble annatto powder is dissolved in 800 ml of water and added to the cellulose suspension. The mass is heated to boiling and 25 g of sodium chloride is added to aid in the dyeing of the cellulose. The suspension is stirred for ten minutes, filtered, the cake washed with water and then washed with dilute acetic acid. The cake is then dried at 50° C. in a hot air oven to obtain a powdered natural pigment of red-orange color suitable for substitution for FD&C Yellow No. 6 Aluminum Lake.

EXAPLE IV 100 g cellulose is suspended in 1500 ml of water at room temperature. 25 g of a grape skin extract (anthocyanins) is added and the pH adjusted to 1.2 with hydrochloric acid. The suspension is then stirred for one hour, filtered and washed with pH 1.2 water. It is then air dried at room temperature to obtain a powdered natural pigment of bluish-red appearance.

EXAMPLE V 100 g of finely powdered corn starch is suspended in 1800 ml of water. 50 g of a 30% (W/V) aluminum chloride solution in water is added to the corn starch suspension and the suspension heated to 50° C. 10 g of curcumin is dissolved in 800 ml of water containing 3.2 g of sodium hydroxide to form a dye solution. The dye solution is then added in a fine stream to the corn starch suspension while stirring the suspension rapidly. Stirring is continued until all the curcumin is attached to the corn starch particles (60 minutes). The slurry is filtered, washed with water, and dried at 50° C. in a hot air oven to obtain a powdered natural dye pigment that simulates and may be substituted for FD&C Yellow No. 5 Aluminum Lake.

EXAMPLE VI

Pharmaceutical tablets are made in accordance with the invention by placing pharmaceutical forms comprising a substrate containing a medicament into a coating pan, making a color dispersion by mixing 15 g of natural dye pigment of Example I and 10 g of titanium dioxide with 75 g of simple syrup, U.S.P., further diluting the dispersion by adding 900 g of simple syrup, U.S.P., rotating the coating pan, repeatedly adding portions of the diluted color dispersion to the coating pan to coat the substrates, and drying and polishing the coated tablets.

We claim:

1. A method of making an edible natural dye pigment for coloring food, drug and cosmetic products comprising:
   suspending a natural water insoluble edible powdered substrate in an aqueous liquid,
   dyeing the suspended powder with an edible natural dye and a dyeing aid or fixing agent, and
   removing the liquid to obtain the dyed powder as a dry powder.

2. The method in accordance with claim 1 in which the suspended powder is cellulose.

3. The method in accordance with claim 1 in which the suspended powder is starch.

4. The method in accordance with claim 1 in which the dye is circumin and the dyeing aid is a water soluble metallic salt.

5. The method in accordance with claim 1 in which the dye is turmeric, and the dyeing aid is a water soluble metallic salt.

6. The method in accordance with claim 1 in which the dye is water soluble annatto powder.

7. The method in accordance with claim 1 in which the dye is grape skin extract.

8. The method of claim 1,
   said powder being water insoluble powders of cellulose, microcrystalline cellulose, cellulose derivatives, ethyl cellulose, starch or starch derivatives,
   the particle size of the powder particles being in the range of about 1 to 50 microns,
   the amount of the powder being about 2% to 15% (W/V) of the amount of the water,
   the edible natural dye being curcumin, turmeric, or an anthocyanin such as those contained in commercial grape skin extract,
   mixing said dyeing aid or fixing agent into the powder suspension to fix the dye onto the powder particles,
   adding the dye to the powder suspension slowly while stirring the powder suspension,
   continuing the stirring after all the dye has been added for a sufficient period of time to fix the dye to the powder,
   filtering the suspension to recover the dyed powder, washing the dyed powder with water and drying it to obtain the natural dye pigment having a particle size in the range of about 1 to 50 microns, said drying being carried out in a mechanical convection oven at a temperature of about 40° to 50° C.

9. The method of claim 1, including suspending 100 g. of finely divided powdered cellulose in 1800 ml. of water, dissolving 15 g. of aluminum sulphate powder in the cellulose suspension as said dyeing aid of fixing agent, heating the suspension to about 50° C., dissolving 5 g. of turmeric in 1800 ml. of ethyl alcohol to form a dye solution, adding the dye solution in a fine stream to the cellulose suspension while stirring the suspension rapidly, continuing said stirring until all the turmeric is attached to the cellulose particles, filtering the slurry, washing the slurry with water, and drying the slurry at about 50° C. in a hot air oven to obtain a powdered natural dye pigment of yellow-orange color.

10. The method of claim 1, including suspending 100 g. of finely powdered cellulose in 1800 ml. of water, dissolving 10 g. of water soluble annatto powder in 800 ml. of water, adding the annatto powder solution to the cellulose suspension, heating the mass to boiling, adding 25 g. of sodium chloride as said dyeing aid or fixing agent, stirring the suspension for 10 minutes, filtering the suspension, washing the resulting cake with water and then washing it with dilute acidic acid, drying the cake at about 50° C. in a hot air oven to obtain a powdered natural pigment of red-orange color suitable for substitution for FD&C Yellow No 6 Aluminum Lake.

11. The method of claim 1, including suspending 100 g. of cellulose powder in 1500 ml. of water at room temperature, adding 25 g. of a grape skin extract, anthocyanins, to the suspension, adjusting the pH of the suspension to about 1.2 by adding a sufficient amount of hydrochloric acid as said dyeing aid or fixing agent, stirring the suspension for about 1 hour, filtering the suspension, washing the filtered cake with water at a pH of about 1.2, air drying the filtered cake at room temperature to obtain a powdered natural pigment of bluish-red appearance.

12. A pigment comprising a natural water insoluble edible powder dyed with an edible natural dye and a dyeing aid or fixing agent.

13. A pigment in accordance with claim 12 in which the powder is powdered cellulose.

14. A pigment in accordance with claim 12 in which the powder is powdered microcrystalline cellulose.

15. A pigment in accordance with claim 12 in which the powder is starch.

16. A pigment in accordance with claim 12 in which the dye is curcumin.

17. A pigment in accordance with claim 12 in which the dye is turmeric.

18. A pigment in accordance with claim 12 in which the dye is annatto.

19. A pigment in accordance with claim 12 in which the dye is a grape skin extract.

* * * * *